(12) United States Patent
Lee et al.

(10) Patent No.: US 8,127,516 B2
(45) Date of Patent: Mar. 6, 2012

(54) METHOD FOR PREPARING RAPIDLY DISINTEGRATING FORMULATION FOR ORAL ADMINISTRATION AND APPARATUS FOR PREPARING AND PACKING THE SAME

(75) Inventors: Chang Hyun Lee, Yongin-si (KR); Jong Soo Woo, Suwon-si (KR); Hong Gi Yi, Suwon-si (KR); Kyeong Soo Kim, Suwon-si (KR); Ho Taek Yim, Yongin-si (KR)

(73) Assignee: Hanmi Pharm. Co., Ltd. (KR)

( * ) Notice: Subject to any disclaimer, the term of this patent is extended or adjusted under 35 U.S.C. 154(b) by 0 days.

(21) Appl. No.: 12/654,572

(22) Filed: Dec. 23, 2009

(65) Prior Publication Data

US 2010/0105783 A1 Apr. 29, 2010

Related U.S. Application Data

(63) Continuation of application No. PCT/KR2008/003623, filed on Jun. 25, 2008.

(30) Foreign Application Priority Data

Jun. 27, 2007 (KR) .................. 10-2007-0063757

(51) Int. Cl.
B65B 63/08 (2006.01)
(52) U.S. Cl. ............... 53/127; 53/560; 53/559
(58) Field of Classification Search ............ 53/127, 53/560, 561, 559, 454; 424/465, 464, 473
See application file for complete search history.

(56) References Cited

U.S. PATENT DOCUMENTS

| | | | |
|---|---|---|---|
| 3,885,026 A | 5/1975 | Heinemann et al. | |
| 4,134,943 A | 1/1979 | Knitsch et al. | |
| 4,506,495 A * | 3/1985 | Romagnoli | 53/559 |
| 4,747,250 A * | 5/1988 | Rossi | 53/511 |
| 4,909,722 A * | 3/1990 | Wakayama et al. | 425/384 |
| 5,178,878 A | 1/1993 | Wehling et al. | |
| 5,459,980 A * | 10/1995 | Kenney et al. | 53/450 |
| 5,462,427 A * | 10/1995 | Kramer | 425/231 |
| 5,522,505 A * | 6/1996 | Giovannone | 206/462 |
| 5,631,023 A | 5/1997 | Kearney et al. | |
| 5,976,577 A | 11/1999 | Green et al. | |
| 6,024,981 A | 2/2000 | Khankari et al. | |
| 6,327,835 B1 * | 12/2001 | Trebbi | 53/53 |
| 6,425,422 B1 * | 7/2002 | Trebbi | 141/67 |
| 6,748,721 B2 * | 6/2004 | Kodai | 53/453 |
| 7,153,118 B2 * | 12/2006 | Trebbi et al. | 425/107 |
| 7,677,016 B2 * | 3/2010 | Trebbi | 53/560 |
| 2001/0035431 A1 * | 11/2001 | Runft | 222/168.5 |
| 2006/0134199 A1 | 6/2006 | Suga et al. | |
| 2007/0134318 A1 | 6/2007 | Vidal et al. | |
| 2008/0141621 A1 * | 6/2008 | Funaro et al. | 53/138.1 |

FOREIGN PATENT DOCUMENTS

| | | |
|---|---|---|
| EP | 1 323 417 | 7/2003 |
| JP | 08-019590 | 1/1996 |
| KR | 10-2004-0002839 | 1/2004 |
| KR | 10-2006-0085699 | 7/2006 |
| KR | 10-2007-0057977 | 6/2007 |
| WO | 93/12769 | 7/1993 |
| WO | 99/47126 | 9/1999 |
| WO | 2005/105049 | 11/2005 |

* cited by examiner

*Primary Examiner* — Sameh H. Tawfik
(74) *Attorney, Agent, or Firm* — Bacon & Thomas, PLLC

(57) ABSTRACT

A method and packaging machine for preparing rapidly disintegrating formulations for oral administration are disclosed. The present invention is characterized in that a powdery mixture including a pharmaceutically active ingredient and a sugar or a sugar alcohol powder is filled into a packaging material and, thereafter, the mixture, filled in the packaging material, is heated. The present invention can simply and economically prepare an oral formulation which undergoes rapid disintegration in the oral cavity and provides for high-quality administration to patients.

16 Claims, 7 Drawing Sheets

METHOD FOR PREPARING RAPIDLY DISINTEGRATING FORMULATION FOR ORAL ADMINISTRATION AND APPARATUS FOR PREPARING AND PACKING THE SAME

This application is a Continuation Application of PCT International Application No. PCT/KR2008/003623 filed on 25 Jun. 2008, which designated the United States.

FIELD OF THE INVENTION

The present invention relates to a method and a packaging machine for preparing an oral formulation which undergoes rapid disintegration in the oral cavity, and the rapidly disintegrating formulation prepared thereby.

BACKGROUND OF THE INVENTION

Rapidly disintegrating formulations are conventionally prepared by various methods using lyophilization, a disintegrating agent, a sublimation-like material, humidification or dehumidification.

For example, U.S. Pat. Nos. 5,631,023 and 5,976,577 disclose a formulation obtained by subjecting a drug-containing solution to lyophilization. Such formulations are recently employed in preparing products marketed by Merck, GlaxoWelcome, and Schering-Plough under the trade names of Pepcid™ RPD (a famotidine formulation), Zofran™ zydis (an ondansetron formulation), and Claritin™ RediTabs, respectively. These formulations disintegrate in the oral cavity within 2 to 3 seconds, but the process for preparing them requires the use of special equipments and packaging materials, causing reduced productivity and high manufacturing cost.

In order to solve this problem, International Patent Publication No. WO 99/47126 has suggested a method for preparing a formulation which is free from a residual organic solvent, by compressing an active ingredient together with a water-soluble polymer binder to form a tablet and subjecting the resulting tablet to humidification under a highly humid condition, followed by drying. This method is known as the WOWTAB technique developed by Yamanouchi Pharmaceuticals of Japan. In addition, International Patent Publication No. WO 93/12769 discloses a method for preparing a formulation by placing in a mold a suspension comprising an active ingredient, agar and sugar, and drying the suspension at 30° C. under a pressure of −760 mmHg. However, this method suffers from low productivity and nonuniform product quality.

Alternatively, the Orasolv technique for the preparation of a rapidly disintegrating formulation has been developed by Cima Labs, and disclosed in U.S. Pat. Nos. 5,178,878 and 6,024,981. The marketed product obtained by the Orasolv technique is represented by Zimig™ Rapimelt (a zolmitriptan formulation) marketed by Astrazeneka, but it does not undergo satisfactory oral disintegration and it gives an uncomfortable feeling when administered because of the generation of effervescent gases.

U.S. Pat. No. 3,885,026 teaches a method for preparing a porous tablet by mixing a volatile excipient such as urethane, urea, ammonium carbonate and naphthalene with other tablet components, compressing the mixture to form a tablet, and heating the tablet to remove the volatile excipient.

Further, U.S. Pat. No. 4,134,943 describes a method for preparing a porous tablet by mixing a solvent having a melting point ranging from −30 to 25° C. (e.g., water, cyclohexane, benzene, tert-butanol) with tablet components, cooling the mixture to solidify said solvent, compressing the solid mixture to form a tablet, and removing the solvent therefrom through evaporation. However, such porous tablets may be toxic due to the residual excipient or organic solvent.

As mentioned above, conventional rapidly disintegrating formulations are prepared by forming a tablet comprising a specific material removable by sublimation, evaporation or dehumidification, and then removing the corresponding specific material therefrom, so that they become porous and allow rapid penetration of saliva. However, such conventional formulations having deliberately formed pores suffer from significant deterioration of physical properties or undesired dimensional changes.

Therefore, there is need for developing rapidly disintegrating formulations capable of being easily manufactured and providing comfortable feeling to a patient during the administration without causing problems resulting from above mentioned conventional methods.

SUMMARY OF THE INVENTION

Accordingly, it is an object of the present invention to provide a simple method and a packaging machine for preparing an oral formulation which undergoes rapid disintegration in the oral cavity and provides enhanced patient comfort during administration.

In accordance with one aspect of the present invention, there is provided a method for preparing a rapidly disintegrating formulation for oral administration, comprising: (A) mixing a pharmaceutically active ingredient with a sugar or a sugar alcohol powder to obtain a powdery mixture, and filling the powdery mixture into a packaging material; and (B) heating the mixture filled in the packaging material obtained in step (A) to cure the mixture.

In accordance with another aspect of the present invention, there is provided the rapidly disintegrating formulation for oral administration prepared by said method.

In accordance with still another aspect of the present invention, there is provided a packaging machine for preparing a rapidly disintegrating formulation for oral administration, comprising: a film feeding unit to feed a forming film; a film shaping unit to shape the forming film, thus forming a lower pocket film provided with a pocket having a container shape; a drug material feeding unit to fill or input a powdery mixture or a tablet, formed by pressing the powdery mixture to have a predetermined shape, into the pocket of the lower pocket film; a heating unit to heat the filled mixture or tablet, thus melting and unifying the filled mixture or tablet; and a sealing unit to attach an upper cover film to the lower pocket film.

In accordance with the present invention, an oral formulation which undergoes rapid disintegration in the oral cavity and allows for enhanced patient comfort during administration can be prepared through a single process line in a simple and economical manner, without deterioration of desired physical properties or undergoing undesirable dimensional changes that occur when a conventional method involving a deliberate pore-forming step is used.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE EMBODIMENT

Figure 1:
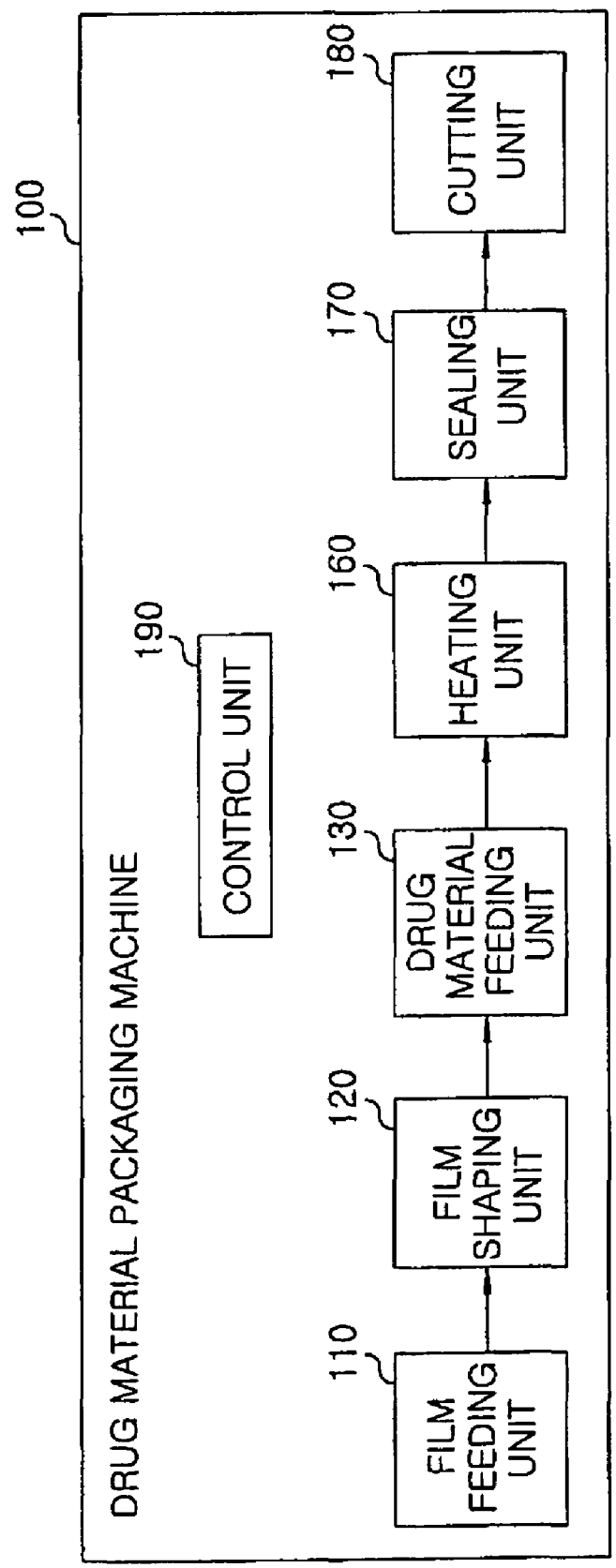
FIG. 1 is a block diagram showing the construction of a packaging machine for preparing a rapidly disintegrating formulation for oral administration, according to an embodiment of the present invention.

Hereinafter, the present invention will be described in detail.

The inventive method is characterized by melt-combining a mixture of a pharmaceutically active ingredient and a sugar or a sugar alcohol having numerous inherent pores through filling the mixture in a packaging material (step (A)) and heating (step (B)) to form a rapidly disintegrating formulation possessing inherent pores, unlike the conventional method which deliberately creates pores through sublimation, evaporation or dehumidification.

The inventive method does not result in deteriorated physical properties of the formulation or undesired dimensional changes, and it is very simple and inexpensive.

<Step (A)>

A composition (mixed powder) used in the preparation of the inventive formulation comprises a pharmaceutically active ingredient and a sugar or a sugar alcohol, and the composition may further comprise a pharmaceutically acceptable additive.

Hereinafter, the components of the inventive composition for a rapidly disintegrating formulation are described in detail as follows:

(1) Pharmaceutically Active Ingredient

①Antifebrile, analgesic or anti-inflammatory agents, e.g., tramadol, ibuprofen, dexibuprofen, aspirin, acetaminophen, indomethacin, sodium diclofenac, ketoprofen, isopropyl antipyrine, phenacetin, flurbiprofen, phenyl butazone, etodolac, celecoxib, etoricoxib and pharmaceutically acceptable salts thereof.

② Anti-gastric ulcer agents, e.g., cimetidine, famotidine, ranitidine, nizatidine, roxatidine and pharmaceutically acceptable salts thereof.

③ Cardiovascular agents or vasodilants, e.g., nifedipine, amlodipine, verapamil, captopril, diltiazem HCl, propranolol, oxprenolol, nitroglycerin, enalapril and pharmaceutically acceptable salts thereof.

④ Antibiotics, e.g., ampicillin, amoxicillin, cephalexin, cefuroxime, cefdinir, cefadroxil, cefprozil, cefpodoxime, cefditoren, cefaclor, cefixime, cefradine, loracarbef, ceftibuten, cefatrizin, cefcarpen, erythromycins, tetracyclines, quinolones and pharmaceutically acceptable salts thereof.

⑤ Antitussives or antiasthmatics, e.g., theophylline, aminopyrine, codeine phosphate, methylephedrine HCl, dextromethorphan, noscapine, salbutamol, ambroxol, clenbuterol, terbutaline, montelukast and pharmaceutically acceptable salts thereof.

⑥ Antiemetics or stomach function-regulating agents, e.g., ondansetron, metoclopramide, domperidone, trimebutine maleate, cisapride, levosulpiride and pharmaceutically acceptable salts thereof.

⑦ Impotence-treating agents, e.g., agents that block the cleavage of nitrogen monoxide, including sildenafil, vadenafil, tadalafil, udenafil and pharmaceutically acceptable salts thereof.

⑧ Dementia-treating agents, e.g., donepezil, galantamine, rivastigmine, acetyl carnitine, memantine, zaliprodene and pharmaceutically acceptable salts thereof.

In addition to the above, other active ingredients may include a benign prostatic hyperplasia-treating agent such as tamsulosin; a migrain-treating agent such as sumatriptan, zolmitriptan and rizatriptan; a psychostimulant; an antibacterial agent; an antihistamine such as loratadine and fexofenadine; an oral antidiabetic such as glimepiride; an allergy-treating agent; a contraceptive; a vitamin; an anticoagulant; a muscle-relaxing agent; a cerebral metabolism-improving agent; an antidiuretic such as torsemide and furosemide; an anticonvulsant such as gabapentine, pregavalin, valproate, topiramate, carbamazepine, lamotrigine and oxcarbazepine; a Parkinson disease-treating agent such as selegiline; an antipsychotic agent such as risperidone, ziprasidone, quetiapine, olanzapine, clozapine and paliperidone; and pharmaceutically acceptable salts thereof; and a biological vaccine.

The active ingredient may be employed in an amount ranging from 0.01 to 90% by weight, preferably 0.02 to 70% by weight, based on the total weight of the powdery mixture.

(2) Sugar or Sugar Alcohol

The sugar or sugar alcohol plays the role of maintaining the shape of the formulation, determines its dissolution rate, and provides sweet taste, solubility, and comfortable touch in the oral cavity. Therefore, it is preferred that the sugar or sugar alcohol is sweet and water soluble. Representative examples thereof include lactose, glucose, sucrose, fructose, mannitol, sorbitol, xylitol, erythritol, ribulose, maltitol, maltose, maltodextrin, paratinose, trehalose, dextrose and a mixture thereof.

The sugar or sugar alcohol may be employed in an amount ranging from 10 to 99.99% by weight, preferably 20 to 95% by weight, based on the total weight of the powdery mixture. When the amount is less than 10% by weight, the sweet and comfortable taste in the oral cavity is not good.

(3) Pharmaceutically Acceptable Additive

In order to enhance both the fluidity of the powdery mixture before filling and the physical properties of the formulation, and also to provide comfortable feeling to a patient during the administration, one more pharmaceutically acceptable additives in addition to the pharmaceutical active ingredient and the sugar or sugar alcohol may be added to the inventive formulation. Examples thereof are a low temperature-melting binding agent, a disintegrator, a lubricant and an excipient (e.g., sweetening agent, filling agent).

The low temperature-melting binding agent functions to maintain the hardness and the shape of the rapidly disintegrating formulation during its handling and storage. The low temperature-melting binding agent may be any one of conventional binding agents and have a melting point of 100° C. or below, of which examples include polyethylene glycol, poloxamer, HCO, glycerine, propylene glycol, glyceride, a derivative thereof, and a mixture thereof. Preferred among them are polyethylene glycol 200, 300, 400, 600, 1000, 1500, 2000, 3000, 4000, 6000, 8000 and 20000, poloxamer 188, 237, 338 and 407, HCO-50, HCO-60, glycerine, glyceryl behenate, glyceryl monostearate, glyceryl monooleate, propylene glycol, medium-chain triglyceride and fatty acid glyceride.

The disintegrator which is used for the more rapid disintegration of the formulation in the oral cavity may be selected from the group consisting of cross-linked polyvinylpyrrolidone, cross-linked carboxymethylcellulose, sodium starch glycolate, calcium carboxymethylcellulose, and a mixture thereof.

The lubricant may be selected from the group consisting of magnesium stearate, talc, silica, sodium stearyl fumarate, valine, sucrose fatty acid ester, hydrogenated castor oil, and a mixture thereof.

As the excipient, a sweetening agent such as aspartame, stevioside, sucralose and acesulfame, or a filling agent such as microcrystalline cellulose, calcium phosphate, calcium carbonate and starch may be used.

Each additive may be used in an amount of 0.01 to 50 parts by weight, preferably 0.1 to 30 parts by weight, based on 100 parts by weight of the mixture.

In the present invention, the pharmaceutically active ingredient, the sugar or sugar alcohol powder, and the optional pharmaceutically acceptable additive may be mixed in accordance with the conventional dry or wet mixing method. All components are uniformly blended in a mixer by the dry mixing method. The wet mixing method comprises subjecting a portion or all of the components to wet granulation and drying the resulting wet granules.

Subsequently, a packaging material, e.g., a lower pocket film which functions as a lower mold for packaging, is filled with a predetermined amount of the mixed powder thus obtained. Suitable for the packaging material may be aluminum, polyvinyl chloride (PVC) or polyvinylidene chloride (PVDC). In particularly, preferred is aluminum which can stand heat ranging from 200 to 1,000° C. In case of employing PVC or PVDC, the filled powder alone may be selectively heated, thereby preventing heat deformation of the packaging material. The lower pocket film for packaging having a particular character or design may be used to obtain the formulation having such character or design as an identification mark. Preferably, after filling, the mixed powder in the packaging material may be tamped using a tamping bar to enhance its uniformity.

<Step (B)>

The mixture filled in the packaging material obtained in the present invention is heated at a temperature ranging from 200 to 1,000° C. for a period of 1 to 60 seconds, preferably 1 to 30 seconds, using radiant heat to cure the filled mixture and obtain a desired rapidly disintegrating formulation. The adherence of the formulation to the packaging material surface may be prevented by adjusting the component ratio of the mixed powder and the heating condition.

In the present invention, the mixture is exposed to a high temperature for a very short period, minimizing heat decomposition of the active ingredient. The exposure time may depend on the nature of each of the used components. A heating apparatus such as a halogen lamp, an infrared-ray (IR) radiator and a heating tunnel may be used, the halogen lamp being preferred.

Then, an upper cover film may be placed to cover the lower pocket film and form a certain shape of the formulation, to complete the encasing of the formulation. The upper cover film may be made of aluminum, but not limited thereto, and it may be any one of conventional materials which is allowable for an easy peeling.

The cured mixture obtained in step (B) may be formulated in the form of a tablet, a pill, a capsule or a dispersant, preferably a tablet, in accordance with the conventional method.

As described above, in accordance with the inventive method, an oral formulation which undergoes rapid disintegration in the oral cavity and provides enhanced patient comfort during administration can be prepared in a simple and economical manner, without deterioration of physical properties or, undesirable dimensional changes that occur when a conventional method involving a deliberate pore-forming step is used.

The following Examples are intended to further illustrate the present invention without limiting its scope.

Example 1

20 mg of famotidine as an active ingredient and 300 mg of xylitol as a sugar alcohol were uniformly mixed, and the mixed powder was filled into a pocket-shaped aluminum film (a lower pocket film). Then, the mixture filled in the pocket film was heated using an infrared-ray lamp at about 800° C. for 6 sec to perform its curing. Then, an aluminum film cover (an upper cover film) was placed on the lower pocket film and sealed, to obtain an inventive rapidly disintegrating formulation tablet.

Example 2

The procedure of Example 1 was repeated except that the filled mixture was heated using an infrared-ray lamp at about 400° C. for 20 sec, to obtain an inventive rapidly disintegrating formulation tablet.

Example 3

The procedure of Example 1 was repeated except that the filled mixture was heated using an infrared-ray lamp at about 600° C. for 15 sec, to obtain an inventive rapidly disintegrating formulation tablet.

Example 4

The procedure of Example 1 was repeated except that the filled mixture was heated using an infrared-ray lamp at about 400° C. for 30 sec, to obtain an inventive rapidly disintegrating formulation tablet.

Example 5

The procedure of Example 1 was repeated except that the filled mixture was heated using an infrared-ray lamp at about 1000° C. for 2 sec, to obtain an inventive rapidly disintegrating formulation tablet.

Examples 6 to 10

The procedure of Example 1 was repeated using each of 300 mg of sorbitol, a mixture of 150 mg of xylitol and 150 mg of sorbitol, 300 mg of maltitol, 300 mg of mannitol and 300 mg of erythritol as the sugar alcohol component, not 300 mg of xylitol, to obtain respective rapidly disintegrating formulation tablets.

Examples 11 to 20

The procedure of Example 1 was repeated using 300 mg of each of lactose, glucose, sucrose, fructose, maltose, paratinose, ribulose, maltodextrin, trehalose and dextrose as a sugar component, without using xylitol as the sugar alcohol component, to obtain respective rapidly disintegrating formulation tablets.

Examples 21 to 45

The procedure of Example 1 was repeated using each of mg of tramadol HCl, 50 mg of ibuprofen, 30 mg of dexibuprofen, 50 mg of aspirin, 50 mg of celecoxib, 20 mg of vadenafil HCl, 5 mg of amlodipine, 50 mg of cefdinir, 50 mg of teofilin, 4 mg of ondansetron, 50 mg of sildenafil, 5 mg of donepezil, 4 mg of galantamine, 0.2 mg of tamsulosin HCl, mg of sumatriptan, 4 mg of montelukast, 10 mg of loratadine, 2 mg of glimepiride, 30 mg of fexofenadine, 5 mg of torsemide, 50 mg of topiramate, 2 mg of risperidone, 10 mg of olanzapine, 2.5 mg of zolmitriptan and 5 mg of montelukast as an active ingredient, not 200 mg of famotidine, to obtain respective rapidly disintegrating formulation tablets.

Examples 46 to 51

The procedure of Example 1 was repeated except that each of 10 mg of PEG 6000, 20 mg of PEG 6000, 40 mg of PEG 6000, 10 mg of poloxamer 188, 20 mg of poloxamer 188 and 40 mg of poloxamer 188 as a lower temperature-melting binding agent was further added to the mixed powder, to obtain respective rapidly disintegrating formulation tablets.

Example 52

The procedure of Example 1 was repeated except that 300 mg of mannitol was dissolved in a mixture of 10 mg of water and 10 mg of ethanol, the solution was subjected to wet granulation, and the resulting wet granules were dried and used as the sugar alcohol, not 300 mg of xylitol, to obtain an inventive rapidly disintegrating formulation tablet.

Example 53

The procedure of Example 1 was repeated except that 150 mg of xylitol and 150 mg of mannitol were dissolved in a mixture of 5 mg of water and 10 mg of ethanol, the solution was subjected to wet granulation, and the resulting wet granules were dried and used as the sugar alcohol, not 300 mg of xylitol, to obtain an inventive rapidly disintegrating formulation tablet.

Example 54

The procedure of Example 1 was repeated except that 50 mg of xylitol and 250 mg of mannitol were dissolved in a mixture of 5 mg of water, 10 mg of ethanol and 5 mg of medium-chain triglyceride (MTC oil), the solution was subjected to wet granulation, and the resulting wet granules were dried and used as the sugar alcohol, not 300 mg of xylitol, to obtain an inventive rapidly disintegrating formulation tablet.

Example 55

The procedure of Example 1 was repeated except that 50 mg of xylitol and 250 mg of mannitol were dissolved in a mixture of 5 mg of water, 10 mg of ethanol and 5 mg of medium-chain triglyceride (MTC oil), the solution was subjected to wet granulation, and the resulting wet granules were dried and used as the sugar alcohol, not 300 mg of xylitol, and that 30 mg of cross-linked polyvinylpyrrolidone as a disintegrator was further added to the mixed powder to obtain an inventive rapidly disintegrating formulation tablet.

Comparative Example 1

Gaster™ oral disintegrating tablet (containing 20 mg of famotidine) commercially available from Dong-A Pharmaceutical Co., Ltd. was used as a comparative formulation. The Gaster™ oral disintegrating tablet was prepared by a conventional WOWTAB technique.

Test Example 1

Disintegration Test

[Disintegration Rate]
The disintegration rate (sec) of the tablet was determined in accordance with the General Test disclosed in Korean Pharmaceutica by dropping it to 5 ml of distilled water (in a spoon) maintained at room temperature and then measuring the time for it to become completely disintegrated.

[Disintegration Rate in a Test Tube]
A 90 mm-diameter filter paper was placed in a 100×10 mm Petri dish. 7 ml of distilled water was poured into the Petri dish and the Petri dish was allowed to be tilt, to complete overall wetting of the filter paper. The disintegration rate (sec) of the tablet in a test tube was determined by placing it on the wet filter paper and then measuring the time for it to get completely wet by a capillary phenomenon.

[Disintegration Rate in an Oral Cavity]
The disintegration rate (sec) of the tablet in an oral cavity was determined by placing it on a healthy male adult's dry tong and then measuring the time for it to become completely disintegrated and dissolved while rubbing.

The disintegration rates and the overall tastes of the tablets obtained in Examples 1 to 55 and Comparative Example were determined, as described above. The results are shown in Table 1.

TABLE 1

|  | Disintegration rate (sec) | Disintegration rate in a test tube (sec) | Disintegration rate in an oral cavity | Taste |
| --- | --- | --- | --- | --- |
| Ex. 1 | 1 | 2 | 2 | Very smooth |
| Ex. 6 | 2 | 3 | 3 | Very smooth |
| Ex. 7 | 2 | 2 | 3 | Very smooth |
| Ex. 8 | 4 | 15 | 20 | smooth |
| Ex. 9 | 3 | 8 | 15 | smooth |
| Ex. 10 | 3 | 7 | 10 | Very smooth |
| Ex. 11 | 5 | 14 | 18 | smooth |
| Ex. 12 | 4 | 8 | 12 | smooth |
| Ex. 13 | 4 | 9 | 12 | smooth |
| Ex. 14 | 4 | 10 | 14 | smooth |
| Ex. 15 | 3 | 8 | 12 | smooth |
| Ex. 16 | 5 | 11 | 22 | smooth |
| Ex. 17 | 4 | 15 | 30 | smooth |
| Ex. 18 | 6 | 20 | 33 | smooth |
| Ex. 19 | 3 | 7 | 10 | smooth |
| Ex. 20 | 3 | 8 | 14 | smooth |

TABLE 1-continued

| | Disintegration rate (sec) | Disintegration rate in a test tube (sec) | Disintegration rate in an oral cavity | Taste |
|---|---|---|---|---|
| Ex. 46 | 1 | 2 | 3 | Very smooth |
| Ex. 47 | 1 | 2 | 3 | Very smooth |
| Ex. 48 | 2 | 5 | 7 | Very smooth |
| Ex. 49 | 2 | 3 | 4 | Very smooth |
| Ex. 50 | 3 | 4 | 6 | Very smooth |
| Ex. 51 | 3 | 5 | 8 | Very smooth |
| Ex. 52 | 1 | 2 | 2 | Very smooth |
| Ex. 53 | 2 | 3 | 3 | Very smooth |
| Ex. 54 | 2 | 2 | 3 | Very smooth |
| Ex. 55 | 1 | 2 | 3 | Very smooth |
| Comp. Ex. 1 | 10 | 56 | 45 | smooth |

As can be seen in Table 1, the inventive tablets obtained in Examples underwent complete disintegration in the oral cavity within 2 to 33 seconds, and the resultant suspensions had satisfactory tastes appropriate for oral administration. In contrast, the Gaster™ oral disintegrating tablet of Comparative Example 1 required more than 40 seconds for complete disintegration in the oral cavity.

Hereinafter, a packaging machine for preparing rapidly disintegrating formulations in a mass production manner using the preparing method of the present invention will be described in detail.

Blister packaging machines are typical pharmaceutical packaging machines. The term blister packaging means a packaging method in which a container-shaped part is formed in a planar film made of synthetic or metal, the container-shaped part is filled with an object, the container-shaped part is covered with a cover which is sealed by adhesion, and it is drawn to a predetermined size and cut, thus forming a unit of a packaging body. In the beginning, in pharmaceutical companies, such blister packaging methods were developed and used to pack a tablet or a capsule in one pack. At present, the blister packaging methods are widely used in confectionery production or in processes of producing cosmetics or household articles. Unlike other packaging methods, in the blister packaging method, because a transparent film is used, products are easily observable, and, because the products are packaged using a film, the shape in which the products are packaged by the film, can be easily modified by modifying the forming mold which, for example, has a shape corresponding to the products or other various shapes. Furthermore, due to the use of a hard film, products can be reliably protected. In addition, when it is desired to use the products, because it is easy to open the products, anybody can use the products. As well, there is an advantage in that the portability is superior.

Such a typical pharmaceutical packaging machine has the following components:

(1) a film feeding unit, for feeding a planar forming film used for manufacturing a lower pocket film for the packaging. The film feeding unit includes an uncoiler, from which a forming film is unwound and is fed, and a draw-off means, which draws a forming film from the uncoiler at a constant speed.

(2) a film shaping unit, including a mold having a shape corresponding to the desired shaped of a product, which works by placing the forming film on the mold, and pressing the forming film by moving a pressing rod downwards, thus forming a depressed pocket in the forming film. The film shaping unit may include a pre-heating part, which pre-heats the forming film to enhance the plasticity of the film.

(3) a content input unit, having a hopper containing contents therein, and inputting contents into the pocket of the film.

(4) a sealing unit, for attaching an upper cover film to seal the lower pocket film, into which the contents are put. The sealing unit includes an uncoiler, around which a cover film is wound in the shape of a roll, and a sealing device.

(5) a cutting unit, for cutting products into a packaging unit. As necessary, the cutting unit may include an embossing device for expressing a product number or date of manufacture, a slitting device for forming a perforated line, and a punching device for conducting a punching operation.

(6) a control unit, installed in the front surface of the machine. The control unit controls the operation of the machine according to the manipulation of a worker. For example, the control unit may be realized by a control panel.

The operation of the pharmaceutical packaging machine having the above-mentioned construction will be described below. The forming film, which has been wound around the uncoiler of the film feeding unit, is fed at a constant speed and is pre-heated by the pre-heating unit of the film shaping unit at a temperature suitable for forming. The forming film is thereafter immediately pressed by the pressing rod, such that pockets for containing contents therein are formed in the forming film, each of the pockets having a shape of the container. As such, the forming film having the pockets becomes the lower pocket film for the packaging. Subsequently, contents (e.g., pills) are inserted into the respective pockets by the content input unit. The lower pocket film, containing the contents therein, is supplied to the sealing unit and is integrated with the upper cover film by pressing, thus sealing the contents. Thereafter, it is cut by the cutting unit into a packaging unit.

In principle, a pharmaceutical packaging machine according to the present invention has the above-mentioned construction and operation, but the detailed shape and function thereof are not limited. In other words, any packaging machine can be used in the present invention, so long as it has a basic blister packaging function.

Figure 2:
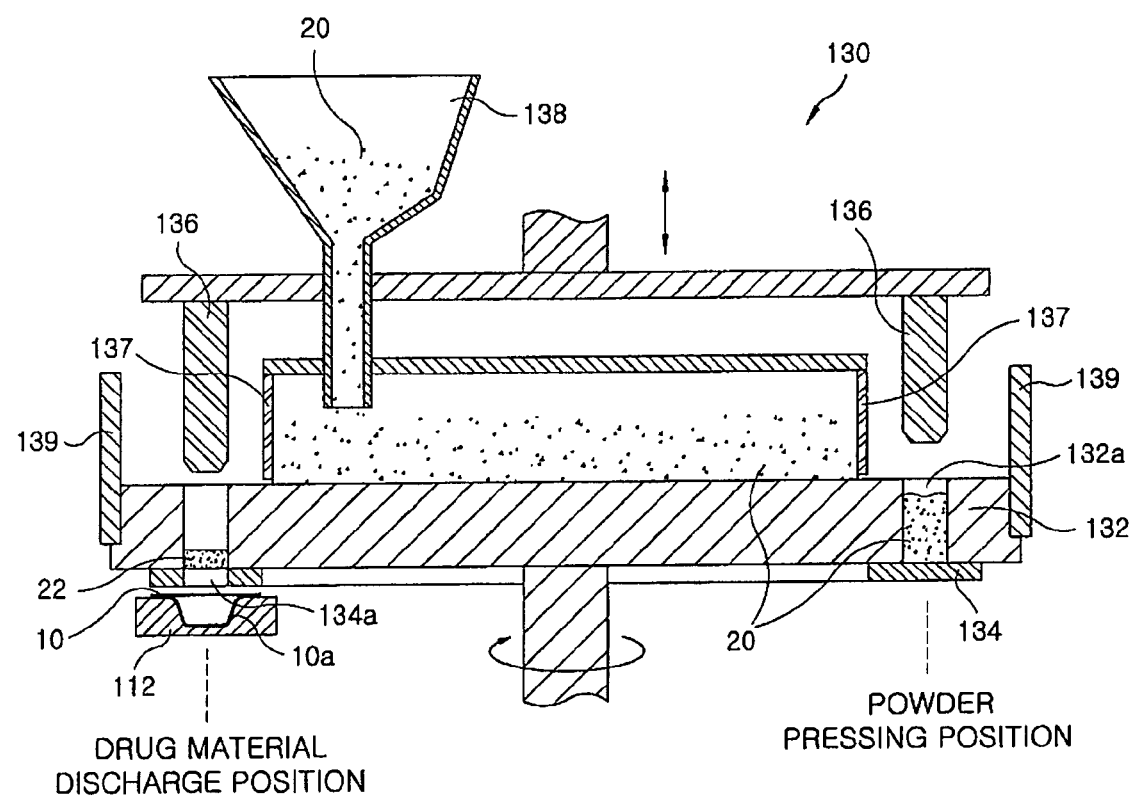
FIG. 2 is a cross sectional view of a drug material feeding unit of the packaging machine for preparing the rapidly disintegrating formulation for oral administration according to the present invention.

FIG. 1 is a block diagram showing the construction of a packaging machine for preparing a rapidly disintegrating formulation for oral administration, according to an embodiment of the present invention. FIG. 2 is a cross sectional view of a drug material feeding unit 130 of the packaging machine.

The packaging machine 100 for preparing the rapidly disintegrating formulation for oral administration according to the present invention has as basic components a film feeding unit 110, a film shaping unit 120, a sealing unit 170, a cutting unit 180 and a control unit 190, similar with the typical pharmaceutical packaging machine. However, the packaging machine 100 further includes the drug material feeding unit 130, which inputs a powdery mixture 20 or a tablet 22, which is formed by pressing the powdery mixture 20 to form a predetermined shape, into a pocket 10a of a lower pocket film 10, unlike the typical pharmaceutical packaging machine having the content input unit. As well, the packaging machine 100 further includes a heating unit 160, which heats the mixture or tablet, input into the lower pocket film 10, so as to melt and unify the mixture or tablet.

Therefore, the arrangement sequentially by position is the film feeding unit 110, the film shaping unit 120, the drug material feeding unit 130, the heating unit 160, the sealing unit 170 and the cutting unit 180.

The drug material feeding unit 130 inputs the powdery mixture 20, which is obtained by mixing a pharmaceutically active ingredient with a sugar or a sugar alcohol powder, or inputs the tablet 22, formed by pressing the powdery mixture 20, into a pocket 10a formed in the lower pocket film 10.

For example, in the drug material feeding unit 130, an appropriate amount of powdery mixture 20 is put into a hole at a powder pressing position and pressed, thus forming a tablet 22 into a predetermined shape. Thereafter, the tablet 22 is input into a pocket 10a of the lower pocket film 10, which has been previously disposed at a position corresponding to a drug material discharge position.

In this embodiment, the drug material feeding unit 130 includes a filling disk 132, which has at least two filling holes 132a which alternate between the powder pressing position and the drug material discharge position. The powdery mixture 20 is piled onto the upper surface of the filling disk 132. The drug material feeding unit 130 further includes a lower disk 134, which is provided under the filling disk 132 and has an opening 134a, which opens the filling hole 132a, disposed at the drug material discharge position, while the filling hole 132a, disposed at the powder pressing position, is closed by the lower disk 134. The drug material feeding unit 130 further includes pressing rods 136, which are provided above respective filling holes 132a so that the pressing rods 136 move downwards into the corresponding filling holes 132a at the same time to press a powdery mixture 20 or discharge a tablet 22 and then move upwards, and a hopper 138, which feeds the powdery mixture 20 onto the filling disk 132.

Here, the filling disk 132 is a circular plate. At least two filling holes 132a are formed through the filling disk 132 at positions spaced apart from each other at regular angular intervals. The filling holes 132a are moved by rotation of the filling disk 132 and are thus alternately positioned above the powder pressing position and the drug material discharge position.

Therefore, after the powdery mixture 20 is fed from the hopper 138 onto the filling disk 132, when the filling disk 132 is rotated and the filling holes 132a are thus respectively moved towards the powder pressing position and the drug material discharge position, some of the piled powdery mixture 20 is naturally drawn into the corresponding filling hole 132a. The filling disk 132 is stopped when this filling hole 132a reaches the powder pressing position. Subsequently, the corresponding pressing rod 136 is moved into this filling hole 132a to press the powdery mixture 20 in the filling hole 132a, thus forming a tablet 22 having a satisfactory unifying force. Thereafter, the pressing rod 136 is moved upwards, and the filling disk 132 is rotated at a predetermined angle such that this filling hole 132a is disposed at the drug material discharge position. Subsequently, the corresponding pressing rod 136 is moved downwards into this filling hole 132a, thus discharging the tablet 22 downwards to the outside of the filling hole 132a. The discharged tablet 22 falls downwards into a pocket 10a of the lower pocket film 10 which is previously disposed at the drug material discharge position.

Of course, because the all pressing rods 136 are moved upwards or downwards at the same time, the powder pressing operation and the tablet discharge operation are conducted at the same time.

In brief, the operation of the drug material feeding unit 130 comprises a step of filling a powdery mixture 20 into a corresponding filling hole, a step of pressing the filled powdery mixture 20, and a step of discharging the tablet 22.

Here, each of the filling step and the pressing step may be performed two or more times to set the amount of contents of the tablet 22 to an appropriate degree. For this, the number of filling holes 132a and the number of pressing rods 136 may be increased by as many as necessary. In this case, the rotating steps of the filling disk 132 are further subdivided.

Of course, in further consideration of the number of the filling and pressing steps, if a required amount of active ingredient of an objective product, that is, a rapidly disintegrating formulation, is relatively small, or if the density of active ingredient is relatively high, the number of steps may be reduced.

Figure 3:
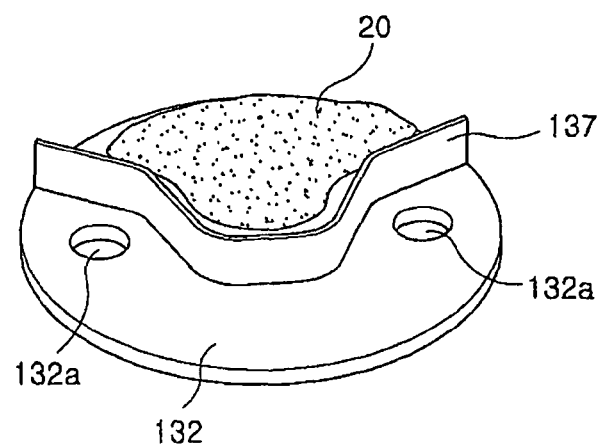
FIG. 3 is a perspective view showing a critical part of the drug material feeding unit of the packaging machine for preparing the rapidly disintegrating formulation for oral administration according to the present invention.

Meanwhile, when forming a tablet 22 at the powder pressing position, when moving the formed tablet 22 from the powder pressing position to the drug material discharge position, or when the tablet 22 is disposed at the drug material discharge position, some powdery mixture 20, which has been around the filling hole 132a having the tablet 22 therein, must be prevented from undesirably entering the filling hole 132a, to enhance the marketability of the tablet 22 and the sealing ability between the upper cover film and the lower pocket film 10. To achieve the above purpose, as shown in FIG. 3, a powder blocking means 137, which extends from a position ahead of the powder pressing position to a position behind the drug material discharge position, may be provided on the upper surface of the filling disk 132. The powder blocking means 137 may have a plate shape.

In the drawings, reference numeral 112 denotes a guide block, which guides movement of the lower pocket film 10, and reference numeral 139 denotes a leakage prevention plate, which prevents the powdery mixture 20 on the filling disk 132 from being undesirably separated from the filling disk 132.

Although the machine of the present invention has been illustrated as being constructed such that powdery mixture 20 is formed into a tablet 22 and then is input into the lower pocket film 10, it may be constructed such that the powdery mixture 20 is directly input into the lower pocket film 10.

Meanwhile, the heating unit 160 heats the mixture or tablet, input into the lower pocket film 10, at a temperature ranging from 200° C. to 1,000° C. for a relatively short period of from several seconds to several tens seconds, thus melting and unifying the mixture or tablet while minimizing decomposition of a pharmaceutically active ingredient. In the case of the powdery mixture, the powdery mixture is melted and unified, thus forming a unified tablet shape. In the case of the tablet, the unifying force thereof can be further increased.

Figure 4:
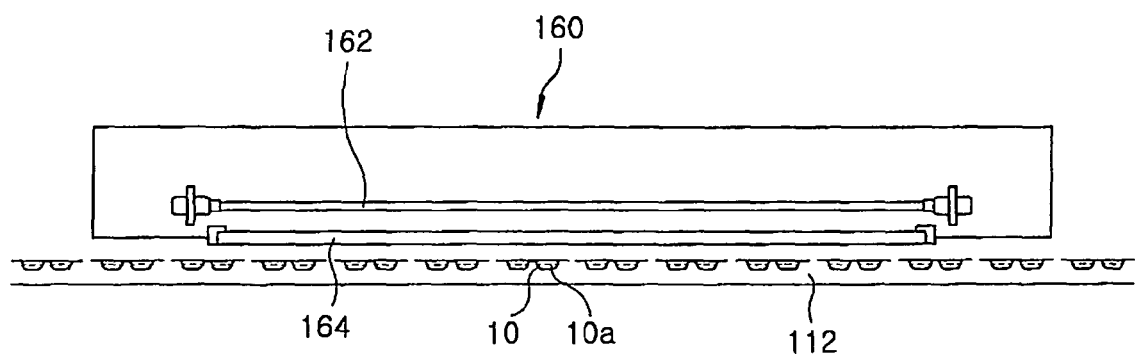
FIG. 4 is a cross sectional view of a heating unit of the packaging machine for preparing the rapidly disintegrating formulation for oral administration according to the present invention.

FIG. 4 is a schematic view showing the construction of a representative example of the heating unit 160.

The heating unit 160 includes a heat generator 162, which is provided above the lower pocket film 10 that is provided on the guide block 112 so as to be movable. The heat generator 162 heats a mixture or tablet, which is filled into the lower pocket film 10, thus melting and unifying the mixture or tablet. The heating unit 160 further includes a shutter 164, which is retractably inserted into a space between the heat generator 162 and the lower pocket film 10 to allow or interrupt the heat transfer from the heat generator 162 to the mixture or tablet, thus controlling the time over which the mixture or tablet is exposed to heat, and making it possible to repeatedly conduct the heating operation.

Here, a halogen lamp, an infrared lamp or the like, which can heat an object to a temperature of 200° C. or more, may be used as the heat generator 162. As necessary, several lamps may be used as the heat generator 162.

Furthermore, a plate, which can cover the lower pocket film 10 and intercept heat transferred from the heat generator 162 to the lower pocket film 10, may be used as the shutter 164. The time for which the lower pocket film 10 is exposed to heat by the retraction of the shutter 164, may be varied according to the kind of ingredients in the drug material and the material used for the lower pocket film 10.

While the lower pocket film 10 is advanced, the opening and closing of the shutter 164 are repeated, so that mixtures or tablets, which are in the lower pocket film 10, are heated for a predetermined exposure time. This operation is repeatedly and continuously conducted.

Figure 5:
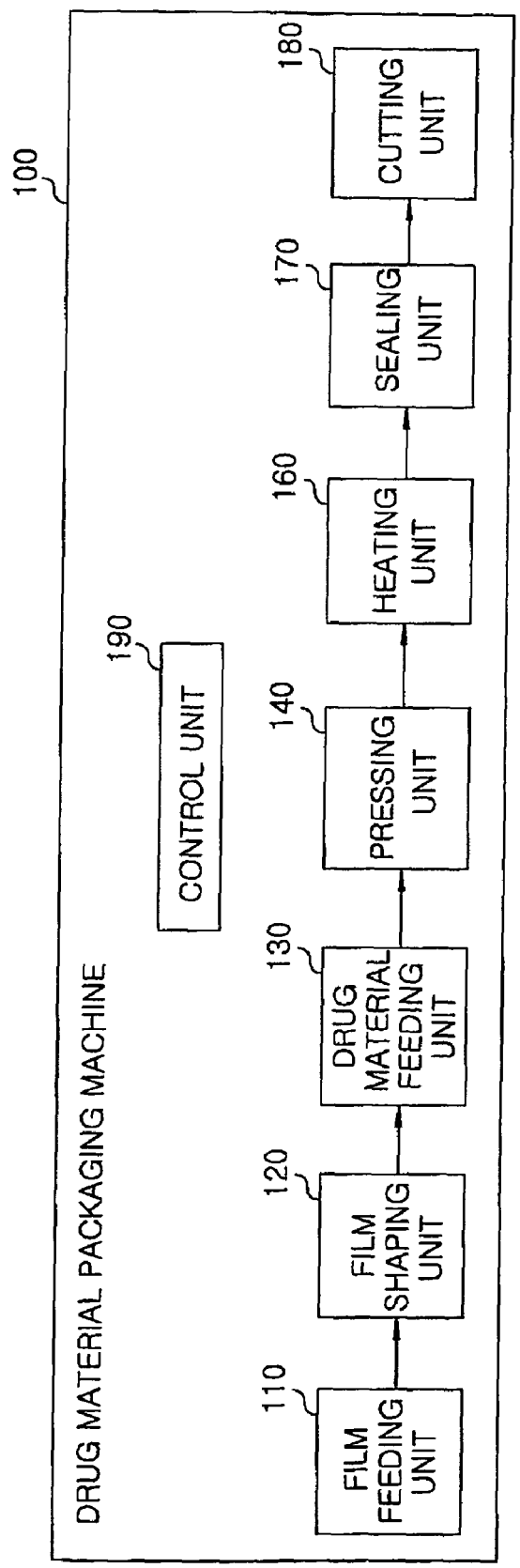
FIG. 5 is a block diagram showing the construction of a packaging machine for preparing a rapidly disintegrating formulation for oral administration, according to another embodiment of the present invention.

Meanwhile, as shown in FIG. 5, the packaging machine 100 for preparing a rapidly disintegrating formulation for oral administration according to the present invention may further include a pressing unit 140, which is provided between the drug material feeding unit 130 and the heating unit 160. The pressing unit 140 serves to press a mixture or tablet, which is input into the corresponding pocket 10*a* of the lower pocket film 10 by the drug material feeding unit 130, thus forming a tablet 22 having a shape corresponding to that of the pocket 10*a*.

Figure 6:
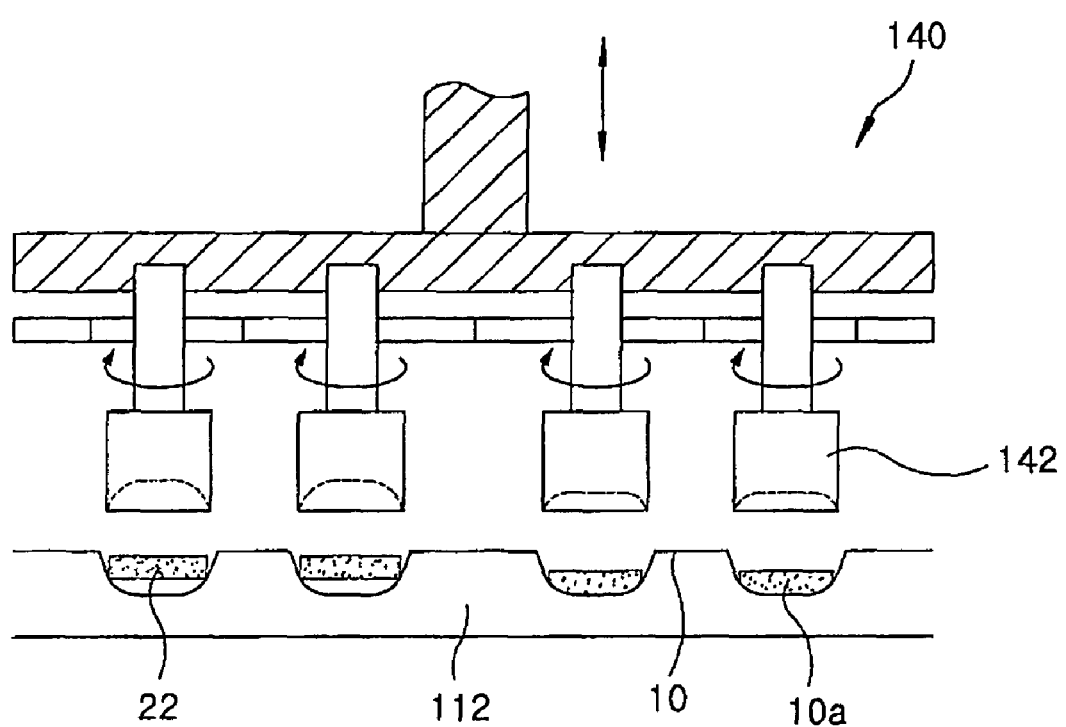
FIG. 6 is a cross sectional view of a pressing unit of the packaging machine for preparing the rapidly disintegrating formulation for oral administration according to the embodiment of FIG. 5.

As shown in FIG. 6, the pressing unit 140 includes tamping rods 142, which are moved downwards into the corresponding pockets 10*a* of the lower pocket film 10 to press mixtures or tablets and then are moved upwards.

Here, to press the mixtures or tablets in multiple steps and thus form the mixtures or tablets into a shape more similar to that of the corresponding pocket 10*a*, several tamping rods 142 having different shapes may be provided at front and rear positions to press the mixtures or tablets. In the drawing, the tamping rods 142 are illustrated as comprising first tamping rods, which primarily press the perimeters of the mixtures or tablets, and second tamping rods, which secondarily press the central portions of the mixtures or tablets.

Furthermore, each tamping rod 142 can be rotated at a fine angle in a state of pressing the corresponding mixture or tablet filled in the pocket film. Therefore, the mixture or tablet can be shaped to have an even shape in the pocket 10*a* without becoming malformed and leaning to one side.

Figure 7:
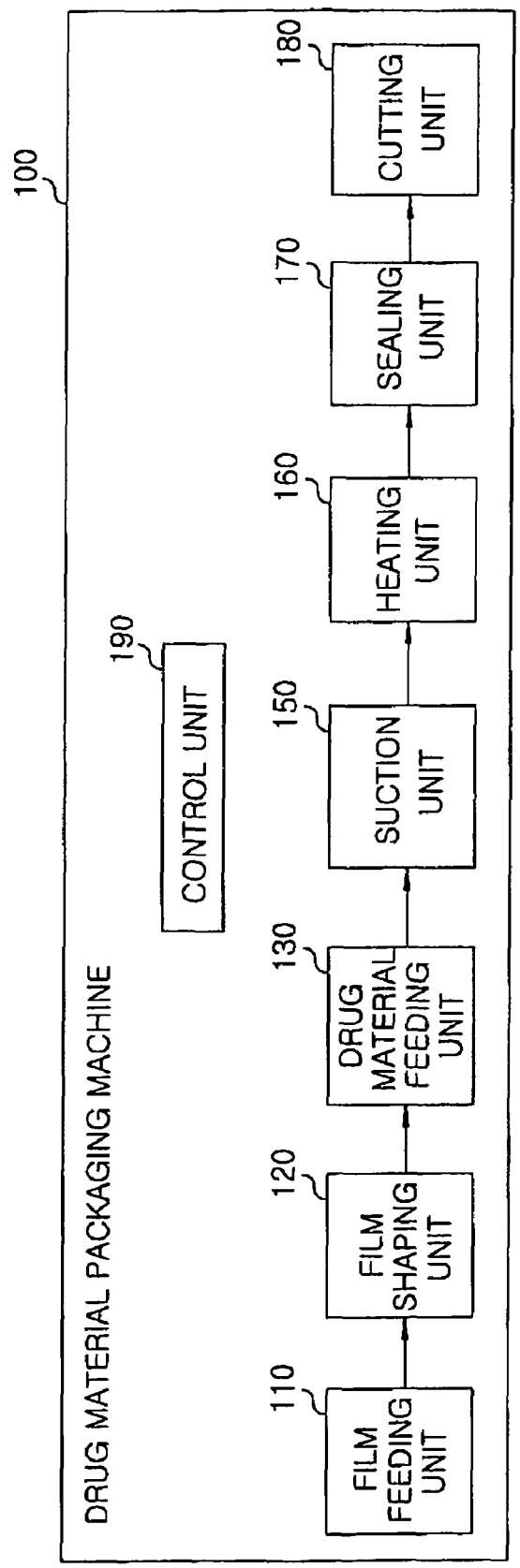
FIG. 7 is a block diagram showing the construction of a packaging machine for preparing a rapidly disintegrating formulation for oral administration, according to still another embodiment of the present invention.

Meanwhile, as shown in FIG. 7, the packaging machine 100 for preparing a rapidly disintegrating formulation for oral administration according to the present invention may further include a suction unit 150, which is provided between the drug material feeding unit 130 and the heating unit 160. The suction unit 150 generates suction pressure on the lower pocket film 10, in which mixtures or tablets are input, thus suctioning and removing undesirable fine powder from the lower pocket film 10, thereby enhancing the marketability of the products and sealing ability of the upper cover film with the lower pocket film 10.

Figure 8:
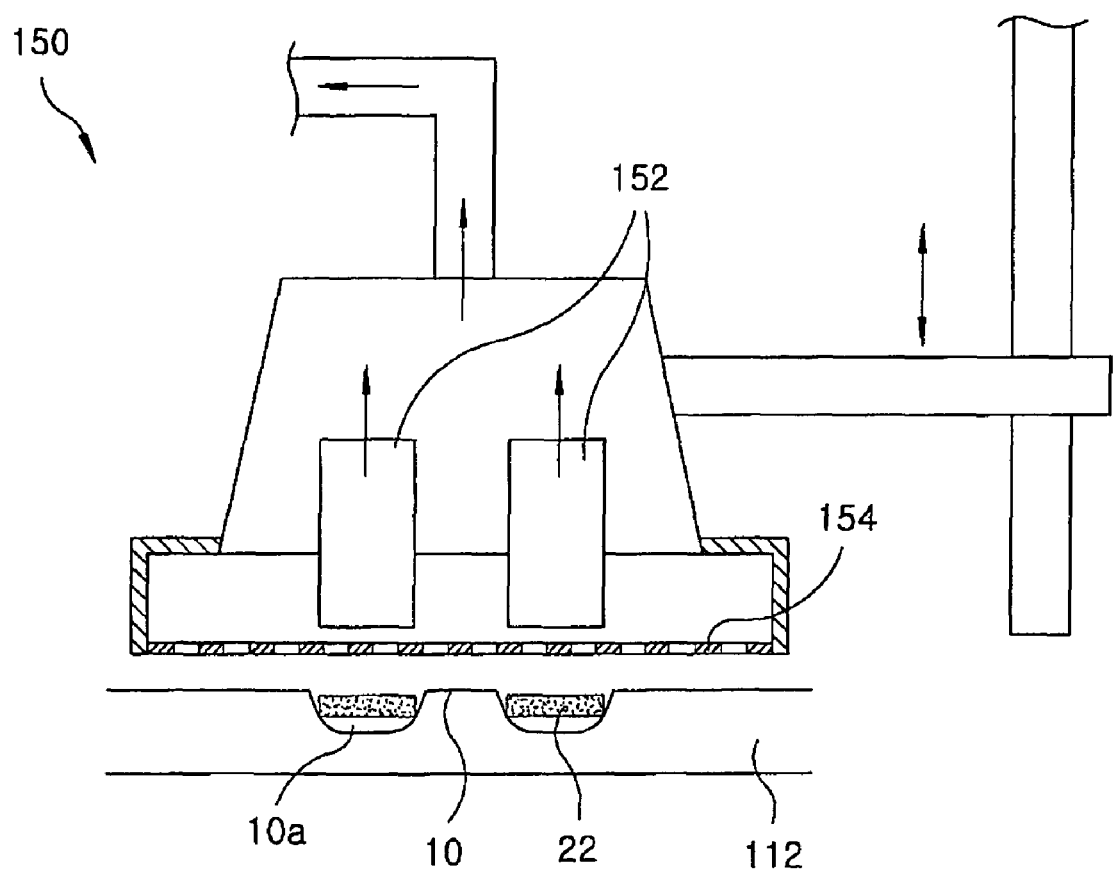
FIG. 8 is a cross sectional view of a suction unit of the packaging machine for preparing the rapidly disintegrating formulation for oral administration according to the embodiment of FIG. 7.

As shown in FIG. 8, the suction unit 150 includes a suction nozzle 152, which is connected to a vacuum utility line in a factory or a vacuum pump so as to generate vacuum suction pressure on the lower pocket film 10, and a screen 154, which is provided at a position between the suction nozzle 152 and the lower pocket film 10 to prevent mixtures or tablets, filled in the pocket film, from being drawn upwards by the vacuum suction pressure.

Here, the suction nozzle 152 may be movable downwards or upwards such that it approaches the lower pocket film 10 or moves away therefrom.

The overall operation of the packaging machine 100 for preparing a rapidly disintegrating formulation for oral administration according to the present invention having the above-mentioned construction will be described below.

First, a forming film is fed from the film feeding unit 110 at a constant speed. The forming film is pre-heated and pressed by the film shaping unit 120 such that pockets 10*a* having container shapes are formed in the forming film, thus forming the lower pocket film 10.

Thereafter, powdery mixtures or tablets are input into the corresponding pockets 10*a* of the formed lower pocket film 10 by the drug material feeding unit 130. The mixtures or tablets filled in the pocket film are pressed in the corresponding pockets 10*a* of the lower pocket film 10 by the pressing unit 140, thus forming tablets 22 having shapes corresponding to that of the pockets 10*a*.

Subsequently, undesirable fine powder, which has been on the lower pocket film 10, is eliminated by vacuum pressure of the suction unit 150.

The mixtures or tablets in the lower pocket film 10 are thereafter heated by the heating unit 160, so that each mixture or tablet is melted and unified to guarantee a reliable unifying force, thereby being formed into a rapidly disintegrating formulation for oral administration.

Subsequently, the lower pocket film 10, containing the rapidly disintegrating formulations for oral administration, is pressed to the upper cover film by the sealing unit 170 and is thus sealed, thus completing the packaging operation. Thereafter, the product is cut by the cutting unit 180 into a predetermined packaging unit.

Finally, the rapidly disintegrating formulation product, which has been packaged, is slowly cooled at room temperature in the packaged state.

As such, rapidly disintegrating formulations for oral administration can be conveniently and economically prepared using mass production through the single process line.

In the present invention, although the heating process has been illustrated as being conducted using the heating unit 160 at a middle step in the packaging process, the heating process may be conducted after the process of attaching the upper cover film to the lower pocket film has been conducted, that is, after the packaging process has been completed. For this, after the process of packaging the rapidly disintegrating formulation products has completed, the products may be supplied into a heating chamber such that the products are separately heated.

While the invention has been described with respect to the above specific embodiments, it should be recognized that various modifications and changes may be made to the invention by those skilled in the art which also fall within the scope of the invention as defined by the appended claims.

What is claimed is:

1. A packaging machine for preparing a rapidly disintegrating formulation for oral administration, comprising:
    a film feeding unit to feed a forming film;
    a film shaping unit to shape the forming film, thus forming a lower pocket film provided with a pocket having a container shape;
    a drug material feeding unit to fill or input a powdery mixture or a tablet, formed by pressing the powdery mixture to have a predetermined shape, into the pocket of the lower pocket film;
    a heating unit to heat the filled mixture or tablet filled in the lower pocket film, thus melting and unifying the filled mixture or tablet; and
    a sealing unit to attach an upper cover film to the lower pocket film.

2. The packaging machine according to claim 1, further comprising:
    a cutting unit to cut a packaging material, formed by attaching the upper cover film to the lower pocket film, into a predetermined unit; and
    a control unit for operation control.

3. The packaging machine according to claim 2, wherein the powdery mixture further comprises a pharmaceutically acceptable additive selected from a group consisting of a low temperature-melting binding agent, a disintegrator, a lubricant, an excipient, and a mixture thereof.

4. The packaging machine according to claim 1, wherein the powdery mixture comprises a pharmaceutically active ingredient and a sugar or a sugar alcohol powder.

5. The packaging machine according to claim 1, wherein the drug material feeding unit comprises:
- a filling disk having at least two filling holes, which are respectively and alternately disposed at a powder pressing position and at a drug material discharge position, the filling disk allowing the powdery mixture to be piled on an upper surface thereof;
- a lower disk provided under the filling disk to open the filling hole disposed at the drug material discharge position and close the filling hole disposed at the powder pressing position;
- pressing rods provided above the respective filling holes, the pressing rods moving downwards into the corresponding filling holes simultaneously to press a powdery mixture, which is filled in the filling hole disposed at the powder pressing position, and discharge a tablet, which is in the filling hole disposed at the drug material discharge position; and
- a hopper to feed the powdery mixture onto the filling disk.

6. The packaging machine according to claim 5, wherein the filling disk is rotated, and the piled powdery mixture is fed into the corresponding filling hole during the rotation of the filling disk.

7. The packaging machine according to claim 5, wherein the powder pressing position comprises at least two powder pressing positions, so that the feeding and pressing of the powdery mixture are conducted in multiple steps.

8. The packaging machine according to claim 5, wherein the drug material feeding unit further comprises:
- powder blocking means provided on the filling disk to prevent additional powdery mixture from entering the filling holes, the powder blocking plate extending from a position ahead of the powder pressing position to a position behind the drug material discharge position.

9. The packaging machine according to claim 1, wherein the heating unit comprises:
- a heat generator to heat the mixture or tablet, filled in the lower pocket film; and
- a shutter to retractably enter a space between the heat generator and the lower pocket film, thus controlling a time period over which the mixture or tablet is exposed to heat.

10. The packaging machine according to claim 1, further comprising:
- a pressing unit to press the mixture or tablet, which is input into the pocket of the lower pocket film by the drug material feeding unit, thus shaping the mixture or tablet into a shape corresponding to a shape of the pocket.

11. The packaging machine according to claim 10, wherein the pressing unit comprises:
- a tamping rod to move downwards into the pocket of the lower pocket film and move upwards after pressing the mixture or tablet.

12. The packaging machine according to claim 11, wherein the tamping rod of the pressing unit comprises at least two tamping rods provided in series to consecutively press the mixture or tablet at least two times.

13. The packaging machine according to claim 12, wherein each of the tamping rods of the pressing unit is rotated after moving downwards into the pocket of the lower pocket film to press the mixture or tablet filled in the pocket, such that the mixture or tablet is evenly shaped in the pocket.

14. The packaging machine according to claim 1, further comprising:
- a suction unit to generate a suction pressure on the lower pocket film, thus suctioning and removing undesirable fine powder from the lower pocket film.

15. The packaging machine according to claim 14, wherein the suction unit comprises:
- a suction nozzle to generate a vacuum suction pressure on the lower pocket film; and
- a screen provided at a position between the suction nozzle and the lower pocket film to prevent the mixture or tablet, filled in the pocket film, from being drawn upwards by the vacuum suction pressure.

16. The packaging machine according to claim 1, wherein the heating unit is provided above the lower pocket film.

* * * * *